United States Patent [19]

Deibig et al.

[11] 4,192,021

[45] Mar. 11, 1980

[54] BONE REPLACEMENT OR PROSTHESIS ANCHORING MATERIAL

[75] Inventors: Heinrich Deibig, Frankfurt am Main; Helmut Heide, Schwalbach; Roland Reiner, Eschborn; Kari Koster, Lorsbach, all of Fed. Rep. of Germany

[73] Assignee: Batelle-Institut e.V., Frankfurt am Main, Fed. Rep. of Germany

[21] Appl. No.: 796,165

[22] Filed: May 12, 1977

[30] Foreign Application Priority Data

May 12, 1976 [DE] Fed. Rep. of Germany ....... 2620890
May 12, 1976 [DE] Fed. Rep. of Germany ....... 2620891

[51] Int. Cl.² .......................... A61F 1/24; C08H 1/06
[52] U.S. Cl. .......................... 3/1.9; 106/161; 128/92 C
[58] Field of Search .................. 106/161; 427/2; 128/92 C, 92 R; 3/1.9

[56] References Cited

U.S. PATENT DOCUMENTS

| | | | |
|---|---|---|---|
| 3,443,261 | 5/1969 | Battista et al. | 106/161 |
| 3,713,860 | 1/1973 | Auskern | 427/2 |
| 3,767,437 | 10/1973 | Cruz | 106/161 |
| 3,787,900 | 1/1974 | McGee | 106/35 |
| 3,867,190 | 2/1975 | Schmitt et al. | 427/2 |
| 4,032,993 | 7/1977 | Coquard | 128/334 R |

*Primary Examiner*—Theodore Morris
*Attorney, Agent, or Firm*—Fisher, Christen & Sabol

[57] ABSTRACT

Bone replacement or prosthesis anchoring material on the basis of sintered calcium phosphates which consists of a mixture of calcium phosphates with low or high-molecular-weight organic substances. More specifically, the anchoring material consists of a mixture of calcium phosphates composed of CaO and $P_2O_5$ in a quantitative ratio of 2:1 to 4:1 with biodegradable polymers in a ratio of 10:1 to 1:1 of phosphate to polymer and is implantable as a solid body. A method for the production of the material wherein calcium phosphate with a porosity of 15 to 30 volume percent is used and its pores are filled by impregnation with polymer material.

15 Claims, No Drawings

BONE REPLACEMENT OR PROSTHESIS ANCHORING MATERIAL

BACKGROUND OF THE INVENTION

1. Field of this Invention

The invention relates to a completely or partially resorbable bone replacement or prosthesis anchoring material on the basis of sintered calcium phosphates.

2. Prior Art

The bone replacement or prosthesis materials presently used are either autologous, homoiologous or heterologous bone transplants or implantable parts of metal, metal compounds, polymers or ceramics. However, all these materials have disadvantages when used for the purpose under consideration. The use of autologous bone grafts implies a double operative procedure combined with considerable postoperative pain for the patient. Homoiologous and heterologous bone grafts, metals, polymers and aluminium oxide ceramic are frequently encapsulated by connective tissue, which prevents bone growth in direct contact to the implant and thus favours loosening of the implant. Further material-dependent reactions are inflammations and foreign-body reactions. In addition, the structure of the above materials as well as that of glass ceramic do not enable resorbable phases to be incorporated, although this would be desirable because it would increase the surface area of the ingrowth region and thus lead to durable implant-bone tissue attachment. Another drawback is to be seen in the fact that re-working of the prosthesis during operation is practically impossible.

While the calcium phosphate ceramic satisfies the requirements of the formation of an intimate bone connection between prosthesis and bearing bone or adjacent bone tissue and that of resorbability of the prosthetic material, this ceramic material is not sufficiently functionally loadable and can be re-worked only to a limited extent.

DESCRIPTION OF THIS INVENTION

Therefore, it is the object of the present invention to overcome the above drawbacks and to create a partially or completely resorbable, implantable material on the basis of sintered calcium phosphates, which leads to a functionally loadable joint between the bone tissue and the implant and in addition enables the bone replacement to be re-worked and adjusted to the individual conditions during the operation. Furthermore, the implant should be mechanically stable and permit regeneration of the natural tissue after the implantation.

It has been found that this aim of the present invention can be achieved in a very advanced manner by means of the bone replacement or prosthesis anchoring material on the basis of sintered calcium phosphates of this invention which is characterized by such material consisting of a mixture of calcium phosphates with low-or high-molecular-weight organic substances.

The bone replacement or prosthetic device can be shaped from the material according to the present invention as block or prosthesis blank and optimally adapted to the given conditions by the surgeon or his assistants during the operation by sawing, cutting, drilling or milling. Both the inorganic and the organic constituents of the material covered by the present invention are resorbable and therefore are gradually replaced by endogenic bone tissue.

In the case under consideration the material consists of a mixture of calcium phosphates composed of CaO and $P_2O_5$ in a quantitative ratio of 2:1 to 4:1 with biodegradable polymers in a ratio of 10:1 to 1:1 of phosphate to polymerizate. It is also possible, however, to implant the material according to the present invention as a completely or partially resorbable, kneadable, plastic material. In this case the material consists of a mixture of calcium phosphate with soft, plastic, bioresistant polymerizates, or with the solution of such a polymer in organic solvents or with soft, plastic, resorbable organic materials at a quantitative ratio between 5:1 and 1:1.

According to an advantageous embodiment of the present invention, the calcium phosphate contained in the plastic material consists of CaO and $P_2O_5$ powder or grains in a quantitative ratio of about 3:1 with grain sizes between 0.3 and 2 mm.

The bioresistant polymer may be a plastic material which cures after implantation by cross-linking or polymerization. On the other hand, however, the polymer may also be dissolved in a solvent, e.g., alcohol, acetone or dimethyl sulfoxide, which is soluble in blood serum. Suitable biodegradable polymers include in particular natural polymers, collagen, fibrinogen and synthetic polymerizates, cyanoacrylate, polyglycolide, polyactide, their copolymers, esters of polymer polyols and their cross-linked products.

The resorbable material may be a polymer or a solution of a polymer. Preferred examples are polyesters of glycolic acid or lactic acid, polyamides of $\alpha$-amino acids, unmodified or modified natural polymers, such as gelatin or starch.

Other resorbable materials which are particularly suited include low-molecular-weight or oligomeric substances or solutions of these substances. In many cases it is favorable to use such low-molecular-weight substances which have a low or moderate serum solubility, such as triglycerides of high alkanecarboxylic acids or esters of polyhydroxy compounds.

Depending on its composition, the material according to the present invention may remain plastic or cure after implantation. It can be used for both temporary and permanent bone replacement. The degree of resorption of the implanted material and its replacement by newly formed endogenic tissue or ingrowth by endogenic tissue depends on the organic constituents used. The objective is in any case to achieve partial replacement or peripheral or complete ingrowth of the implant by endogenic tissue.

According to an advantageous embodiment of the present invention, solid materials are provided to have continuous pores or pore ducts with an average diameter between 0.6 and 2 mm, at least in the border zone between implant and bone tissue. This defined open macropore structure of the implant results in an increase in the contact area between bone and implant and thus in a wider connection zone. This encourages ingrowth of bone tissue into the prosthetic material and leads to steady resorption of the entire prosthetic material, which is at the same time replaced by the bone tissue.

According to another embodiment of the present invention, the material claimed here is calcium phosphate with a porosity of 15 to 30 volume percent, whose pores are filled with the polymer material by impregnation. Solidification of the polymer inside the pores can be achieved either by polymerization of the material in the pores of the calcium phosphates or by evaporation of the solvent.

In addition, it is possible according to the present invention to mix the calcium phosphate in powder form with the melt or solution of a polymer or with prepolymers, then to give the mixture the desired shape, and finally to cure the polymer by cooling, evaporation of the solvent, or polymerization.

Further characteristic features, benefits and potential applications of the present invention can be gathered from the following description of further details on the basis of specific examples illustrating the method of production and the composition of the material according to the present invention.

EXAMPLE 1

A block of calcium phosphate 8×8×3.5 cm in size was covered in a desiccator with 500 ml of butyl α-cyanoacrylate and impregnated with the monomers by evacuating and aerating three times. After polymerization of the cyanoacrylate it was found by gravimetry that about 9.3 percent, related to the total volume, consists of polymer. To avoid too rapid polymerization, the inorganic starting material used in this process should be very dry. It is also possible to impregnate the calcium phosphate block by sucking through the cyanoacrylate and thus to polymerize it to give a composite. In this case the calcium phosphate block is clamped between two glass cylinders, one of which is filled with monomer solution, while the other is evacuated.

EXAMPLE 2

A block of calcium phosphate 8×8×3.5 cm in size was evacuated in an autoclave together with 400 g of glycolide powder which contained 0.1 percent zinc chloride, then heated to a temperature of 200° C. and subsequently kept at this temperature for three hours at a nitrogen pressure of 50 atm.

This procedure ensures that the block is satisfactorily impregnated with the glycolide and a readily workable composite is obtained by polymerization of the glycolide to give polyglycolide. The proportion of polymer in this composite was about 8 percent.

EXAMPLE 3

An intimate mixture of 65 percent of finely ground calcium phosphate and 35 percent of poly-l-lactide was compressed in a mold of 6 cm height and 3 cm diameter at 200° C. under a molding pressure of 5 t to give a cylindrical part. In this case it is possible to vary both the grain size of the calcium phosphate and the calcium phosphate:polymer ratio in a relatively wide range. Because of the high polymer proportion selected, this material differs from those described in examples 1 and 2 in so far as in the in-vitro test the calcium phosphate can be less readily and rapidly eluted from the polymer phase by acid solution.

EXAMPLE 4

To repair a skull cap defect, a material according to the present invention, produced as described in example 2, was autoclaved under the usual conditions. The a conical disc was turned from a cylindrical blank of this material and in the surgery adapted to the skull defect by means of a scalpel. Subsequently the resultant part was inserted under moderate pressure, and the wound was closed by suturing the periosteum and the scalp.

After a period of three weeks, osteoid tissue had grown into the surface pores of the implant. Resorption of the calcium phosphate had started, whereas the polyglycolide was not yet resorbed. Bone growth and resorption of the material took place simultaneously. The polymer and the calcium phosphate were tissue-compatible; foreign-body reactions were not observed.

The time required for resorption and complete penetration of the prosthesis with bone tissue depends on the size of the implant and its macroporosity.

In addition to the above properties of the material according to the present invention, such as tissue compatibility, functional loadability and workablity, it is of advantage that the material stimulates the bone tissue to grow on the surface of the ceramic. As it is possible to produce the prosthesis such that it has a macropore structure and orientation adapted to the physiological requirements, bone growth can be induced to proceed in a desirable preferred direction.

EXAMPLE 5

Collagen was treated with a Ca(OH)$_2$ solution; after removal of Ca(OH)$_2$ a 70-percent collagen paste was obtained. This paste was intimately mixed with Ca-phosphate powder which had been moistened in a ratio of 1:2 with glutaraldehyde in an amount of 5 percent of its weight and cured by heating at 60° C. for four hours to give a readily workable composite.

EXAMPLE 6

A collagen paste produced according to the method described in example 5 was intimately mixed with 5 weight of percent paraformaldehyde, then compressed at 100° C. into a porous Ca-phosphate block with a porosity of about 30 percent, and cured by heating at 50° C. for five hours.

EXAMPLE 7

To synthesize the calcium-phosphate component of the material according to the present invention, a homogeneous powder mixture is in this case produced from the compounds CaHOP$_4$ and calcium carbonate (CaCO$_3$), both analytical grade, and pressed to large, cylindrical tablets. These tablets are then sintered in a kiln at 1200° C. for 3 hours, so that the compound tricalcium phosphate is formed almost completely according to the formula.

$$2\ CaHPO_4 + CaCO_3 \rightarrow Ca_3P_2O_8 + H_2O \uparrow + CO_2 \uparrow.$$

This sintered product is ground, again compressed, and sintered at 1500° C. for one hour. Now the material consists of a mixture of α- and β-tricalcium phosphate and residual amounts of a vitreous calcium-phosphate phase in a specific quantitative ratio which had been found most suitable with regard to tissue compatibility and resorbability. This material is again ground and screened in a size between about 0.3 and 0.7 mm.

In this form it is combined with the polymer component in the following manner:

50 g of trilaurin (triglyceride of lauric acid) is processed in a kneader at 50° to 55° C. together with 50 g of the above-described calcium phosphate to give a homogeneous plastic material. The resultant product is sterilized and packed under sterile conditions.

The surgeon receives the material packed in small portions.

The plastic material produced by the above method is used for tamponing a bone cavity after resection of a cyst: after removal of the cyst and the usual preparation of the implant bed, the cavity is firmly packed with the plastic material, all recesses being filled. To improve the processability of the material, it can be heated to 50° C. After smoothing of the surface, the periosteum is sutured over the implant.

Depending on the size of the implant, the replacement material is ingrown by newly formed connective tissue and osteoidic tissue within a period of several days to weeks. Simultaneous with this process, resorption of the prosthetic material takes place. The newly formed bone tissue is in direct contact with the calcium phosphate without an intermediate fibrous layer; The implant, depending on its size, is resorbed and replaced by sound bone tissue within a period of several weeks.

EXAMPLE 8

First, calcium phosphate is produced by the method described in example 7. Then a mixture of 50 g of calcium phosphate, 10 g of polymethyl methacrylate and 0.2 g of benzoyl peroxide is gas-sterilized and packed under sterile conditions (component 1). Component 2 consists of 40 g of methyl methacrylate (mixed with 100 ppm of hydroquinone) and 0.2 g of N,N-dimethyl-p-toluidine.

Prior to the use of the material, the two components are mixed to give a paste which cures completely within 15 to 20 minutes.

In the case of complicated operations and extended handling times of the pasty material, products with lower peroxides and amine contents can be used.

In the present example the zygomatic arch was replaced by such material. After surgical preparation of the two ends of the zygomatic arch, the material produced by the above-described method was molded into the desired shape. For viable bone pieces supplied with blood, a loadable support was formed from the pasty material. The surgeon has sufficient time for handling the material, as it cures only after about 15 minutes.

The histological findings are analogous to those obtained in the case of example 7, with the only exception that the organic consistuents are not resorbed.

What is claimed is:

1. Bone replacement of prosthesis anchoring material on the basis of calcium phosphates and organic materials characterized in that said material consists of a mixture of sintered calcium phosphates composed of CaO and $P_2O_5$ in a quantitive ratio between 2:1 and 4:1 with at least one low-molecular-weight biodegradable or bioresistant organic material, which has a molecular weight of up to 800, or at least one high-molecular-weight biodegradable or bioresistant organic material or a mixture thereof and wherein it is implantable as a solid body or as a kneadable pasty substance, whereby the quantitive ratio of the calcium phosphate to the organic materials is between 10:1 and 1:1 for a solid body and is between 5:1 and 1:1 for a pasty substance.

2. Bone replacement or prosthesis anchoring material as claimed in claim 1 wherein said material has continuous pores or pore ducts, which have an average width between 0.6 and 2 mm, in the surface area of the implant.

3. Bone replacement or prosthesis anchoring material as claimed in claim 1 wherein biodegradable organic substance is a polyester of glycolic acid, lactic acid, a polyamide of an α-amino acid, an unmodified natural polymer, a modified natural polymer, or a low-molecular-weight or oligomeric substance or solution of these substances, and wherein the low-molecular-weight substance has a low to moderate serum solubility and has a molecular weight of up to 800.

4. Bone replacement or prosthesis anchoring material as claimed in claim 3 wherein said low-molecular-weight substance has a molecular weight of up to 800 and is a triglyceride of a $C_{12}$–$C_{18}$ alkane carboxylic acid or an ester of a polyhydroxy compound.

5. Method for the production of said bone replacement or prosthesis anchoring material as claimed in claim 1 comprising mixing calcium phosphate in powder form with the melt or solution of a biodegradable polymer or with liquid prepolymers, working the mixture into the desired shape and solidifying the polymer by further polymerization, cooling or evaporation of the solvent.

6. Method as claimed in claim 1 wherein the biodegradable organic substance is a polyester of glycolic acid, lactic acid, a polyamide of an α-amino acid, an unmodified natural polymer, a modified natural polymer, or a low-molecular-weight or oligomeric substance or solution of these substances, and wherein the low-molecular-weight substance has a low to moderate serum solubility and has a molecular weight of up to 800.

7. Method as claimed in claim 6 wherein said low-molecular-weight substance has a molecular weight of up to 800 and is a triglyceride of a $C_{12}$–$C_{18}$ alkane-carboxylic acid or an ester of a polyhydroxy compound.

8. Method for the production of said bone replacement or prosthesis anchoring material as claimed in claim 1 comprising filling the pores of a calcium phosphate body, which has continuous pores or pore ducts with an average width between 0.6 and 2 mm in the surface area of the implant and has a porosity of 16 to 30 volume percent, with the melt or solution of a biodegradable polymer or with liquid prepolymers, and solidifying the polymer by further polymerization in the pores of the calcium phosphate or by evaporation of the solvent.

9. Method as claimed in claim 1 wherein the biodegradable organic substance is a polyester of glycolic acid, lactic acid, a polyamide or an α-amino acid, an unmodified natural polymer, a low-molecular-weight or oligomeric substance of solution of these substances, and wherein the low-molecular weight or oligomeric substance of solution of these substances, and wherein the low-molecular-weight substances has a low to moderate serum solubility and has a molecular weight of up to 800.

10. Method as claimed in claim 9 wherein said low-molecular-weight substance has a molecular weight of up to 800 and is a triglyceride of a $C_{12}$–$C_{18}$ alkane-carboxylic acid or an ester of a polyhydroxy compound.

11. Method for the production of said bone replacement of prosthesis anchoring material as claimed in claim 1 comprising mixing calcium phosphate in powder or granular form with a grain size between 0.3 and 2 mm with soft, plastic biodegradable or bioresistant organic materials or polymers or with a solution of a polymer, which, if necessary, cures after the implantation of the plastic material by crosslinking or by further polymerization.

12. Method as claimed in claim 11 wherein the polymer is dissolved in a solvent which is soluble in blood serum.

13. Method as claimed in claim 12 wherein said solvent is alcohol, acetone or dimethyl sulfoxide.

14. Method as claimed in claim 1 wherein the biodegradable organic substance is a polyester of glycolic acid, lactic acid, a polyamide of an α-amino acid, an unmodified natural polymer, a modified natural polymer, or a low-molecular-weight or oligomeric substance or solution of these substances, and wherein the low-molecular-weight substance has a low to moderate serum solubility and has a molecular weight of up to 800.

15. Method as claimed in claim 14 wherein said low-molecular-weight substance has a molecular weight of up to 800 and is a triglyceride of a $C_{12}$–$C_{18}$ alkane-carboxylic acid or an ester of a polyhydroxy compound.

* * * * *